(12) United States Patent
Liu

(10) Patent No.: US 9,770,480 B2
(45) Date of Patent: Sep. 26, 2017

(54) PRODUCING A TOPICAL SOLUTION COPOSITION

(75) Inventor: Kay Liu, San Marino, CA (US)

(73) Assignee: Shantel Medical Supply Corp., Arcadia, CA (US)

( * ) Notice: Subject to any disclaimer, the term of this patent is extended or adjusted under 35 U.S.C. 154(b) by 1598 days.

(21) Appl. No.: 11/837,735

(22) Filed: Aug. 13, 2007

(65) Prior Publication Data

US 2009/0047372 A1 Feb. 19, 2009

(51) Int. Cl.

| | |
|---|---|
| *A61K 36/87* | (2006.01) |
| *A61K 8/34* | (2006.01) |
| *A61K 8/81* | (2006.01) |
| *A61K 8/97* | (2017.01) |
| *A61Q 19/00* | (2006.01) |

(52) U.S. Cl.
CPC .............. *A61K 36/87* (2013.01); *A61K 8/347* (2013.01); *A61K 8/8147* (2013.01); *A61K 8/97* (2013.01); *A61Q 19/004* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 6,124,364 A * | 9/2000 | Breton et al. | |
| 6,238,678 B1 * | 5/2001 | Oblong et al. | ................ 424/401 |
| 6,280,712 B1 * | 8/2001 | Ansmann et al. | |
| 2006/0078530 A1 * | 4/2006 | Liu | |
| 2007/0003644 A1 * | 1/2007 | Randhava et al. | ............ 424/766 |
| 2007/0009455 A1 * | 1/2007 | Kim et al. | ...................... 424/62 |

OTHER PUBLICATIONS

Wikipedia: "Pinot noir". Downloaded from the world wide web on Aug. 15, 2010.*
Wikipedia contributors. Magenta. Wikipedia, The Free Encyclopedia. Downloaded Sep. 15, 2013. Retrived from http://simple.wikipedia.org/wiki/Magenta, pp. 1-8.*
Burns, J et al., J. Agric. Food Chem. (2001); 49:5797-5808. Extraction of phenolics and changes in antioxidant activity of red wines during vinification.*
MacNeil (The Wine Bible. Workman Publishing: New York, 2001, Print. Exerpt, pp. 30-35).*
"Portfolio Winery" website (https://web.archive.org/web/20060324003616/http://www.portfoliowinery.com/winery.html—internet archived version from Mar. 2006).*

* cited by examiner

*Primary Examiner* — Susan Hoffman
(74) *Attorney, Agent, or Firm* — Alberto Q. Amatong, Jr.; Amatong McCoy LLC

(57) ABSTRACT

A process of providing a topical solution which includes a high level of resveratrol by using a low temperature mixing process. The low temperature mixing process uses key ingredients that mix at low temperatures eliminating the risk of heat oxidation that creates Radical Oxygen Species that bind with resveratrol.

19 Claims, 3 Drawing Sheets

PRODUCING A TOPICAL SOLUTION COPOSITION

TECHNICAL FIELD

The present invention is generally related to a topical solution composition that revitalizes layers of the skin.

SUMMARY

The primary objective of the present invention is to produce a skin topical solution composition that revitalizes damaged skin. The production of the topical solution is accomplished by providing a grape extract and adding vitamins that are capable of increasing the pH and an aqueous solution with a carbomer base where the carbomer base acts as an emulsion stabilizer and where the grape extract is subjected to a fermentation and mixing process that yields the highest conversion of cis- and trans-piceid (a glucoside-analog of resveratrol) into cis- and trans-resveratrol.

The topical solution comprises a number of ingredients depending on if the desired final form of the topical solution is a gel or a cream. At a minimum the ingredients for the topical solution must include a grape extract, vitamins that are capable of increasing the pH and an aqueous solution with a carbomer base where the carbomer acts as an emulsion stabilizer and where the grape extract is subjected to a fermentation and mixing process that yields the highest conversion of cis- and trans-piceid (a, glucoside-analog of resveratrol) into cis- and trans-resveratrol.

BACKGROUND

Figure 1:
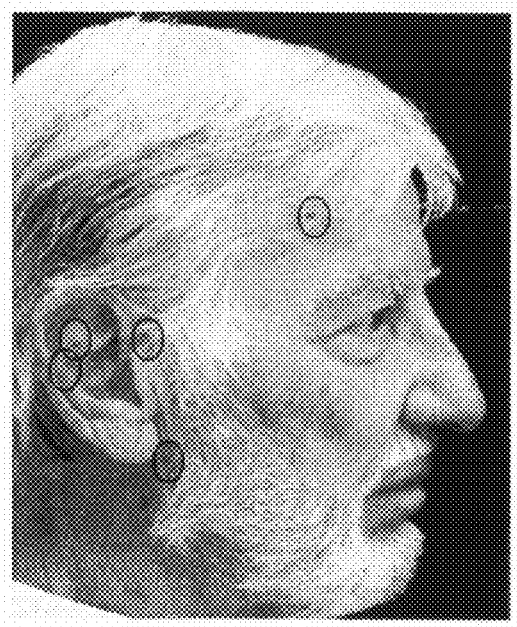
FIG. 1 Image of subject before and after using the skin lotion
Figure 1:
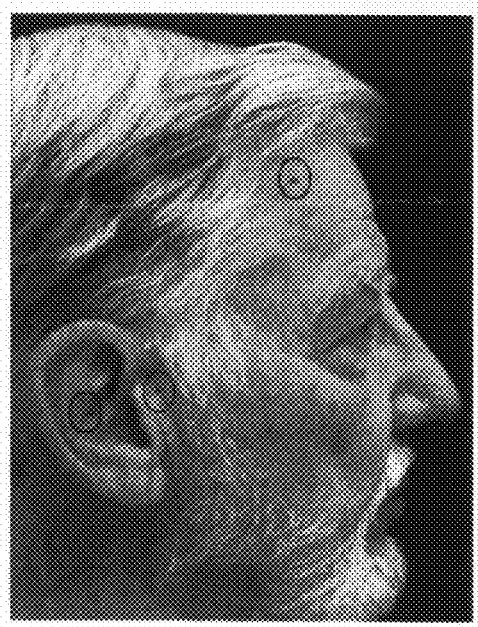

The present invention relates to revitalizing layers of the skin which have been damaged by the environment. More specifically sunlight exposure and particularly ultraviolet radiation can cause a variety of skin changes and damages such as premature aging, and skin cancer. There are three main types of UV radiation, UVA, UVB, and UVC. UVC has the shortest wavelength. UVA on the other hand has the longest wavelength. However, as with any electromagnetic energy, the shortest wavelength is the most susceptible to obstruction while the longest wavelength is the least. UVC for example is almost completely blocked by the ozone layer in our atmosphere, while UVB penetrates the atmosphere relatively unobstructed and causes damage in the outer layer of the skin. UVB, however, does not penetrate glass. UVA, on the other hand, can penetrate glass and deeper into the skin to cause skin damage.

On a cellular level, UV radiation can cause collagen breakdown, creation of free radicals, interfere with DNA repair, and suppress the immune system's ability to survey and destroy cancerous cells. Of these damaging effects, perhaps the most significant is the creation of free radicals.

Oxygen molecules normally exist in stably bonded pairs. Free radicals are created when ionizing energy like UV radiation strikes a stable, paired oxygen molecule splitting its paired electron bonding, resulting in two single oxygen molecules. These two oxygen molecules each have one unpaired valence electron that is very reactive inside human tissues and cells. These free radical oxygen molecules react with organic molecules in the connective tissue and cells stealing electrons away from structures that require those electrons for stable bonds. This causes damage to enzymes, DNA's, collagen structures and cell wall stability and permeability. Damage to these cellular structures can cause for example: DNA mutations (that lead to cancerous behavior); suppression of enzymatic functions that regulate cellular signaling, apoptosis, immune functions, as well as, DNA repair.

One well known skin condition that occurs as a result of prolonged, cumulative effect of sun exposure is Actinic Keratosis, (AK's). AK's are by far the most common skin lesion with malignant potential on the skin. These lesions develop in a stepwise progression from subclinical skin changes to overt, invasive Squamous Cell Carcinoma, (SCC). If left untreated, these AK lesions have 1 per 1000 per year chance of becoming cancerous.

Clinically, AK's present with a range of characteristics. They can be barely perceptible to rough, elevated hyperkeratotic plagues several centimeters in diameter. The base may be light or dark, tan, pink, red, or a combination of these. Most typically though, they appear as multiple discrete lesions that are small crusty, scaly or crumbly bump or horn on an erythematous base.

Histologically, AK's share features with SCC. The histological characteristics are as follows: AK's are located in the epidermis and show hyperkeratosis with intermittent large parakeratotic nuclei and occasional mitotic figures; keratinocyte atypia along the basal layer; spongiosis in the immediate suprabasalar layer; budding of the basal layer keratinocytes into the dermis; perivascular inflammation and solar elastosis.

Treatment of AK's typically consists of surgical destruction. The difficulty with surgical destruction is that it is difficult and impractical to treat a large area of the skin that has large number of lesions.

DETAIL DESCRIPTION

The use of the present invention which, was further proven in studies performed by an independent research investigator at the Palo Alto Medical Foundation, greatly improves or completely resolves AK lesions. Furthermore since the present invention consists of a topical solution that is topically applied it is not limited to impracticalities of treating large areas of the skin like surgical destruction.

Recently there has been significant interest in the medical and health industry generated about red wine. Red wine is known to have several biologically active compounds; most of them belong to a family known as polyphenols. Polyphenols are of great interest to the medical and health industry because of the potential benefits to human health. These compounds possess antioxidant, anti-inflammatory, and anticarcinogenic properties that are the focus of many current research investigations.

Polyphenols are a group of heterogeneous compounds with four main classes: flavonols, stilbenes, flavones, and phenolic acids. Such compounds include, for example, proanthocyanidins, quercitin, anthocyanins, and resveratrol and its glucoside analogs). Studies involving these four main classes suggest that of the polyphenols, resveratrol may be the most effective in anticancer property.

Resveratrol exist as a cis-isomer and a trans-isomer. It falls under a class of polyphenols known as stilbenes. A glucoside analog of resveratrol is found naturally, to varying levels, in the skin of grapes in its isomeric forms called cis- and trans-piceid.

In the past, it was not known how to produce a grape extract to include in a topical solution where the grape extract was not damaged in the production process. Also, it was not known how to produce a grape extract that yields high levels of resveratrol. Finally due to fact that red wine and red wine's extract naturally has an extremely low pH (between 1.0 and 2.0) it was not known how to produce a topical solution that would not inflame or burn the skin.

In the present invention the grape extract is mixed by using a cold process which does not damage the grape extract, parameters in the fermentation process are heavily controlled to maintain a specific rage that yields high levels of resveratrol and certain ingredients are used in the production process that increases the natural pH level of red wine thereby allowing one to produce a topical solution with an acceptable pH and with the highest quantity of active polyphenols.

The topical solution composition of the present invention includes a grape extract which is produced predominantly from grapes that are rich in magenta color. We have found that grapes that are rich in magenta color yield the highest amount of resveratrol due to the high tannin content of the grapes' skin. We have also found that certain vintages like Merlot and Cabernet yield the highest form of resveratrol content because their vintage process includes more parts of the grapes' skin. Furthermore, there is a well known method of testing, growing and producing grapes with high levels of resveratrol.

Figure 3:
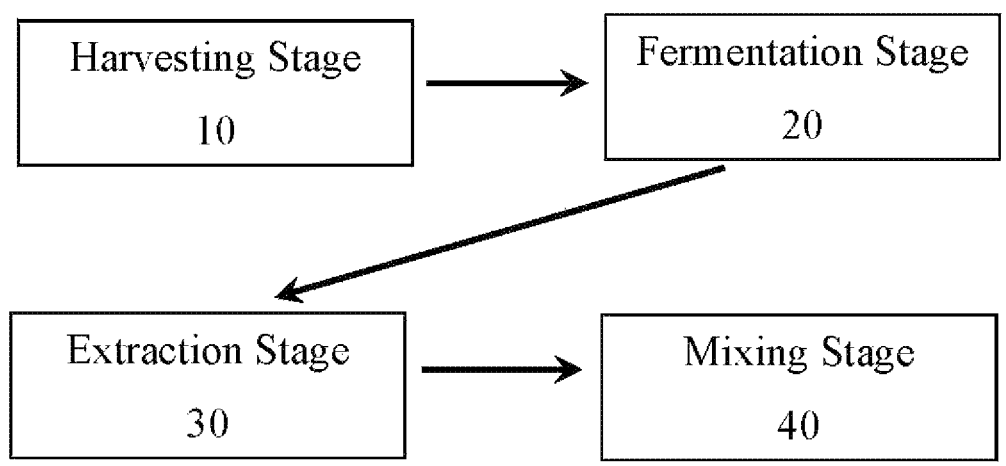
FIG. 3 is a flow chart of a process for developing a topical solution.

The process for developing the topical solution is referenced in the flow chart within FIG. 3 which starts with the harvesting stage (10) where grapes are harvested for their rich magenta color. The grapes are then subjected to a fermentation process named in FIG. 3 as the fermentation stage (20) which is a process in which an agent causes an organic substance to break down into simpler substances. The fermentation process used to produce the grape extract in the present invention includes the addition of yeast as the agent which causes the anaerobic breakdown of the sugar within the grape extract into alcohol. It is important that the fermentation parameters are strictly enforced. Too much fermentation yields an alcohol level that is more than two percent by volume. The increased level of alcohol above two percent by volume is a result that occurs when the fermentation process has begun to break down the Coumaroyl CoA molecule thereby not allowing it to yield the best reaction thereby yielding a long chain molecule. The preferred length of fermentation for the present invention depends on the temperature and humidity and the preferred range is between seven days at a temperature of ninety five degrees Fahrenheit and 80 percent humidity to forty five at a temperature of thirty five degrees Fahrenheit and 30 percent humidity. This range yields the highest conversion of cis- and trans-piceid (a glucoside-analog of resveratrol) into cis- and trans-resveratrol without oxidizing the polyphenols. After the fermentation process the grapes are then subjected to an extraction process which is performed in the extraction stage (30), where the water and ethanol content produced during the fermentation process is slowly removed leaving only the constituents of the grapes behind in a stable powder form.

This powder form of the grape extract is then subjected to the mixing stage (40) where depending if the designed outcome of the topical solution is a gel or cream various ingredients are added. The mixing process is particularly inventive due to the cold process mixing methods employed to mix the powder form of the grape extract into an aqueous solution with a carbomer base. Additional ingredients are then further added and mixed to increase the level of pH. The traditional mixing process uses heat to melt the ingredients thereby allowing the ingredients to adequately mix together. It is well known in the art of producing skin lotions to use high temperatures between 100 and 300 degrees Celsius in order to facilitate the melting and mixing of the ingredients. We have found that the use of high temperatures causes heat-oxidation in the grape extract. Heat oxidation occurs when elevated temperatures increase the activity of oxygen and serves as a catalyst by exothermic reactions for the formation of Radical Oxygen Species (ROS) from oxygen. When anti-oxidants such as resveratrol are exposed to heat-oxidation they bind with the ROS thereby decreasing the amount of resveratrol. In effect, heat-oxidization prematurely reduces or eliminates the anti-oxidant benefits of the grape extract.

In the present invention the mixing process of the grape extract is performed in room temperature between twenty to forty degrees Celsius thereby reducing any oxidation of the polyphenols caused by heat. This low temperature mixing process uses ingredients that are capable of being mixed without the need for increased temperatures.

This limits the types of ingredients one can use to in a skin lotion. We found that the following ingredients and their percentages are most contusive to mixing by use of a cold process when producing a topical solution using the present invention where the topical solution is in the form of a gel:

| Gel | |
| --- | --- |
| Ingredients: | Percentage |
| D. I. Water | 68.10 |
| Red Wine Extract | 5.00 |
| *Aloe Barbensis* Extract | 4.00 |
| Cucumber Extract | 3.00 |
| Hylauronic Acid | 2.50 |
| Isoplene Glycol | 2.00 |
| Tocopherol Acetate | 2.00 |
| Chamomile Extract | 2.00 |
| Jojoba Oil | 2.00 |
| Hydrolyzed Milk Protein | 2.00 |
| Nettle (*Urtica Diolica*) Extract | 0.50 |
| Hydrolyzed Wheat Protein | 0.50 |
| Phytic Acid | 0.50 |
| Wheat Germ Oil | 0.50 |
| Horsetail Extract | 0.50 |
| Centella Assistica Extract | 0.50 |
| Chlorella Vulgaris Extract | 0.50 |
| Hydrolyzed Algin | 0.50 |
| Butylene Glycol | 0.50 |
| Naicinamide | 0.50 |
| Adensosine Triphosphate | 0.50 |
| D-Panthenol (Vitamin B5) | 0.50 |
| Carbomer | 0.20 |
| Xanthan Gum | 0.20 |
| Methylparaben | 0.20 |
| Butylparaben | 0.20 |
| Ethylparaben | 0.20 |
| Propylparaben | 0.20 |
| Triethanolamine | 0.20 |
| | 100.00 |

We also found that the following ingredients are most contusive to mixing by use of a cold process when producing a topical solution using the present invention where the topical solution is in the form of a cream:

| Cream | |
| --- | --- |
| Deionized Water | 62.60 |
| Grape extract | 6.00 |
| Isoprene Glycol | 5.00 |
| Squalane | 4.00 |
| *Santalum Album* Sandalwood Extract | 4.00 |
| Phellodendron Amurense Bank Extract, | |
| *Hordeum Distichon* (Barley) Extract, | |
| Polyglyceryl-2 Stearate | 2.00 |
| Ceteary Methicone (and) Dimethicone (and) Linleic Acid (and) *Glycine Soja* (soybean) Sterol (and) Phospholipids | 2.00 |
| Dimethylopolsiloxane | 2.00 |
| *Chenesis* (Jojoba) Seed Oil | 2.00 |
| Tetrahexyldecyl Ascrobate | 3.00 |
| Tocopheryl Acetate (Vitamin E) | 3.00 |
| Cetyl Alcohol | 1.00 |
| Shea Butter | 1.00 |
| Phenoxyethanol (and) Methylparaben (and) Butylparaben (and) Ethylparaben (and) Propylparaben | 1.00 |
| Bees Wax | 0.50 |
| Cetearyl Glycoside | 0.50 |
| Xanthan Gum | 0.20 |
| Carbomer | 0.2 |
| Total | 100.00 |

It is important a topical lotion have a pH no less than 2.5 and no more than 8.0. If the pH of the topical solution composition is less than a pH of 2.5 or more than a pH of 8.0 the topical solution will burn the skin. The pH level of grape extract is between 1.0 and 2.0 which if applied would burn the skin. Therefore additional materials must be added to increase the pH level. In the present invention a form of vitamin E for example Tocopherol with a pH level between 4.0 and 7.0 is added to the topical solution and a form of vitamin B for example Panthenol with a pH level between 4.0 and 7.0 is added to the topical solution to increase the pH level. Either a form of vitamin E, a form of vitamin B or a form of vitamin E and vitamin B may be used to increase the level of pH of the grape extract. Furthermore it is well known in the art that both vitamin E and vitamin B act to moisturize the skin thereby further complimenting the topical solution. Also, vitamin E and vitamin B are compatible with the cold process of the present invention.

The topical solution composition comprises: 0.1% to 50.0% of Grape extract of the total mixture and 0.1% to 50.0% of an aqueous solution with a carbomer base of the total mixture, 0.1% to 50.0% of Vitamin B5, 0.1% to 50.0% of Vitamin E and, 0.1% to 50.0% water of the total mixture.

Figure 2:
FIG. 2 Image of subject before and after using the skin lotion

Results of our clinical study where subjects used the topical solution showed statistically significant improvements in AK's on skin. Each study subject was his/her own control. One side of the face was treated with the topical solution, while the other side was treated with a placebo gel which was simply the vehicle of the first topical gel without the skin lotion. The results show approximately 50%-85% improvement of AK's on the treatment side while the placebo side show little improvement or even progression of AK's. For example, in FIG. 1, the subject's treated side prior to treatment show 5 AK lesions and post-treatment show only 3 AK's. In FIG. 2, the treatment side of this subject showed 5 AK lesions and post-treatment shows only 1 AK lesion. These results were based on gross visual exam by the research investigator whose specialty is dermatology and confirmed by biopsy of skin lesions of the subjects on both sides of their faces.

The reduction of AK lesions after treatment with the skin lotion effectively makes it possible to treat a large area of skin affected with large number of AK's without significant side effects or discontinuation due to discomfort. Also, because our product has a low side effect profile, it can be used as a long-term maintenance product for patients with sun damaged skin to treat any subclinical cellular atypia that may not have been detected yet.

During the fermentation process resveratrol is produced from a Coumaroyl CoA molecule with three Coumaroyl CoA molecules in three successive reduction reactions yielding a long chain molecule called tetraketide with a single benzene ring. Then that molecule is further process in a cyclization process by either the resveratrol synthase or chalcone synthase to yield the final product of resveratrol or quercitin respectively. Our experience with various forms of red wine from a variety of grapes, and length of fermentation has resulted in a product that contains the highest quality of grape extract.

Various embodiments of the invention have been described. These and other embodiments are within the scope of the following claims.

What is claimed is:

1. A method for producing a topical solution in the form of a gel or cream for revitalizing damaged skin, the method comprising the steps of:
    providing grapes having concentrations of resveratrol;
    fermenting the grapes by use of yeast as an agent, wherein said fermenting is performed at a duration between seven days and forty-five days, at a temperature between 35 degrees F. and 95 degrees F., and at a humidity between 30 percent and 80 percent;
    extracting a grape extract from fermented grapes, wherein the amount of alcohol in the grape extract is not more than two percent by volume, whereby water and ethanol are removed to leave grape extract in powder form;
    mixing the grape extract in powder form into an aqueous solution and at a temperature between twenty degrees Celsius and forty degrees Celsius, thereby producing a topical solution in the form of a gel or cream having a pH of less than 2.5; and
    adding vitamins to the topical solution thereby raising the pH of the topical solution to a pH between 2.5 and 8.0; and
    wherein said adding includes adding vitamin B5 or vitamin E to the topical solution to raise the pH of the topical solution.

2. The method of claim 1, wherein the adding step includes adding vitamin B5 and vitamin E to the topical solution to raise the pH of the topical solution.

3. The method of claim 1, wherein the step of providing grapes includes providing grapes of a magenta color.

4. The method of claim 1, wherein the mixing step includes providing an aqueous solution consisting of ingredients that are conducive to mixing in a cold process between twenty degrees Celsius and forty degrees Celsius and wherein adding the vitamins includes adding the vitamins to raise the pH of the solution to a pH between 4.0 and 7.0.

5. The method of claim 1, wherein said mixing includes mixing the grape extract into the aqueous solution with a carbomer base.

6. The method of claim 4, further comprising selecting ingredients from the group of ingredients that are conducive to mixing in a cold process consisting of the following: Carbomer, Isoprene Glycol, Xanthan Gum, and Butylene Glycol; and
wherein the mixing step further includes mixing the grape extract powder into the aqueous solution and with the selected ingredients to produce a topical solution in the form of a gel.

7. The method of claim 1, further comprising the step of selecting ingredients from the group of ingredients consisting of: Isoprene Glycol, Polyglyceryl-2 Stearate, Dimethylpolysiloxane Cetyl Alcohol, Bees Wax, Cetearyl Glucoside, Xanthan Gum and Carbomer, and
wherein the mixing step further includes mixing the grape extract powder with the selected ingredients to produce a topical solution in the form of a cream.

8. The method of claim 1, wherein the step of providing grapes includes selecting grapes from the group of grapes consisting of: merlot; cabernet; and combinations thereof.

9. The method of claim 1, wherein said fermenting includes controlling the duration of fermentation, temperature, and humidity to yield conversion of cis- and trans-piceid into cis- and trans-resveratrol without oxidizing the polyphenols.

10. The method of claim 1, wherein the step of providing grapes includes providing grapes of a magenta color.

11. A method for producing a topical solution in the form of a gel for revitalizing damaged skin, the method comprising the steps of:
providing grapes having concentrations of resveratrol;
fermenting the grapes by use of yeast as an agent;
extracting a grape extract from fermented grapes, whereby water and ethanol are removed to leave grape extract in powder form;
selecting ingredients from the group of ingredients that are conducive to mixing in a cold process consisting of the following: Carbomer, Isoprene Glycol, Xanthan Gum, and Butylene Glycol;
mixing the grape extract in powder form into an aqueous solution and with the selected ingredients and at a temperature between twenty degrees Celsius and forty degrees Celsius, thereby producing a topical solution in the form of a gel having a pH of less than 2.5; and
adding vitamins to the topical solution thereby raising the pH of the topical solution to a pH between 4.0 and 7.0; and
wherein said adding includes adding vitamin B5 or vitamin E to the topical solution to raise the pH of the topical solution;
wherein said aqueous solution comprises 68.10% deionized water and 5.0% grape extract and the following selected ingredients: 4.00% Aloe Barbadensis Extract; 3.00% Cucumber Extract; 2.50% Hyaluronic Acid; 2.00% Isoprene Glycol; 2.00% Tocopherol Acetate; 2.00% Chamomile Extract; 2.00% Jojoba Oil; 2.00% Hydrolyzed Milk Protein; 0.50% Nettle (Urtica Dioica) Extract; 0.50% Hydrolyzed Wheat Protein; 0.50% Phytic Acid; 0.50% Wheat Germ Oil; 0. 50% Horsetail Extract; 0.50% Centella Asiatica Extract; 0.50% Chlorella Vulgaris Extract; 0. 50% Hydrolyzed Algin; 0.50% Butylene Glycol; 0.50% Niacinamide; 0.50% Adenosine Triphosphate; 0.50% D-Panthenol (Vitamin B5); 0.20% Carbomer; 0.20% Xanthan Gum; 0.20% Methylparaben; 0.20% Butylparaben; 0.20% Ethylparaben; 0.20% Propylparaben; and 0.20% Triethanolamine.

12. The method of claim 6, wherein said mixing produces a topical solution comprising: 0.1% to 50.0% of grape extract of the total mixture, 0.1% to 50.0% of an aqueous solution with a carbomer base, 0.1% to 50.0% of Vitamin B5, 0.1% to 50.0% of Vitamin E and, 0.1% to 50.0% water.

13. The method of claim 1, wherein the pH level of the grape extract is between 1.0 and 2.0.

14. The method of claim 1, wherein the topical solution is in the form of a gel, and wherein said aqueous solution comprises deionized water and grape extract and the following selected ingredients: Aloe Barbadensis Extract; Cucumber Extract; Hyaluronic Acid; Isoprene Glycol; Tocopherol Acetate; Chamomile Extract; Jojoba Oil; Hydrolyzed Milk Protein; Nettle (Urtica Dioica) Extract; Hydrolyzed Wheat Protein; Phytic Acid; Wheat Germ Oil; Horsetail Extract; Centella Asiatica Extract; Chlorella Vulgaris Extract; Hydrolyzed Algin; Butylene Glycol; Niacinamide; Adenosine Triphosphate; D-Panthenol (Vitamin B5); Carbomer; Xanthan Gum; Methylparaben; Butylparaben; Ethylparaben; Propylparaben; and Triethanolamine.

15. The method of claim 1, wherein the topical solution is in the form of a gel, and wherein said aqueous solution comprises deionized water and grape extract and one or more of the following selected ingredients: Aloe Barbadensis Extract; Cucumber Extract; Hyaluronic Acid; Chamomile Extract; Jojoba Oil; Hydrolyzed Milk Protein; Nettle (Urtica Dioica) Extract; Horsetail Extract; Centella Asiatica Extract; Chlorella Vulgaris Extract; Niacinamide; Adenosine Triphosphate; and Triethanolamine.

16. The method of claim 1, wherein the topical solution is in the form of a cream, and wherein said aqueous solution comprises deionized water and grape extract and the following selected ingredients: isoprene glycol; squalane; santalum album sandalwood extract; phellodendron amurense bank extract; hordeum distichon extract; polyglyceryl-2 stearate; ceteary methicone; dimethicone; linoleic acid; glycine soja; sterol; phosopholipids; dimethyllopolsiloxane; chenesis seed oil; tetrahexyldecyl ascrobate; tocopheryl acetate; cetyl alcohol; shea butter; phenoxyethanol; methylparaben; butylparaben; bees wax; cetearyl glycoside; xanthum gum; and carbomer.

17. The method of claim 16, wherein said aqueous solution comprises 62.60% deionized water and 6.00% grape extract; 5.00% isoprene glycol; 4.00% squalane; 4.00% santalum album sandalwood extract; 2.00% polyglyceryl-2 stearate; 2.00% dimethicone; 2.00% dimethyllopolsiloxane; 2.00% chenesis seed oil; 3.00% tetrahexyldecyl ascrobate; 3.00% tocopheryl acetate; 1.00% cetyl alcohol; 1.00% shea butter; 1.00% methylparaben; butylparaben; 0.50% bees wax; 0.50% cetearyl glycoside; 0.20% xanthum gum; and 0.2% carbomer.

18. The method of claim 1, wherein the topical solution is in the form of a cream, and wherein said aqueous solution comprises deionized water and grape extract and one or more of the following selected ingredients: squalane; santalum album sandalwood extract; phellodendron amurense bank extract; hordeum distichon extract; sterol; dimethyllopolsiloxane; chenesis seed oil; tetrahexyldecyl ascrobate; and shea butter.

19. The method of claim 1, wherein said fermentation process is conducted to yield a product having an alcohol level no more than 2% by volume and such that resveratrol is produced from Coumaroyl CoA molecule with three Coumaroyl CoA molecules in three successive reduction reactions yielding a long chain molecule followed by a cylcization process by reseveratrol synthase yielding said resveratrol.

* * * * *